US012570599B2

(12) United States Patent
Lochmann et al.

(10) Patent No.: US 12,570,599 B2
(45) Date of Patent: Mar. 10, 2026

(54) PROCESS FOR PREPARING ACYL-CAPPED 3-HYDROXYCARBOXYLIC ACIDS AND THEIR SALTS AND ESTERS

(71) Applicant: KetoLipix Therapeutics GmbH, Hamburg (DE)

(72) Inventors: Dirk Lochmann, Witten (DE); Sebastian Reyer, Witten (DE); Michael Stehr, Witten (DE)

(73) Assignee: KetoLipix Therapeutics GmbH (DE)

( * ) Notice: Subject to any disclaimer, the term of this patent is extended or adjusted under 35 U.S.C. 154(b) by 1017 days.

(21) Appl. No.: 17/618,585

(22) PCT Filed: Jun. 12, 2019

(86) PCT No.: PCT/EP2019/065275

§ 371 (c)(1),
(2) Date: Dec. 13, 2021

(87) PCT Pub. No.: WO2020/249197

PCT Pub. Date: Dec. 17, 2020

(65) Prior Publication Data

US 2022/0315520 A1 Oct. 6, 2022

(51) Int. Cl.
*C07C 69/716* (2006.01)
*C07C 67/02* (2006.01)
*C12N 9/20* (2006.01)
*C12P 7/62* (2022.01)

(52) U.S. Cl.
CPC ............ *C07C 69/716* (2013.01); *C07C 67/02* (2013.01); *C12N 9/20* (2013.01); *C12P 7/62* (2013.01)

(58) Field of Classification Search
CPC ... C12P 7/62; C12N 9/20; C07C 67/02; C07C 69/716
See application file for complete search history.

(56) References Cited

U.S. PATENT DOCUMENTS 7,691,854 B2 4/2010 Gielen-Haertwig et al.

FOREIGN PATENT DOCUMENTS

WO WO-2018115158 A1 * 6/2018 ........... A61K 31/047
WO 2018226732 12/2018

OTHER PUBLICATIONS

Stubbs et al. "On the metabolism of exogenous ketones in humans." Frontiers in physiology 8 (2017): 848 (Year: 2017).*
Irby et al. "Lipid-drug conjugate for enhancing drug delivery." Molecular pharmaceutics 14, No. 5 (2017): 1325-1338 (Year: 2017).*
Schmidt et al., "Katalytische Hydrierung und Hydrokupplung von Acetessigsauresamiden und-estem mit dem Clusteranion [H3Ru4(CO)12]—als Katalysator", Journal of Organometallic Chemistry, Jan. 1, 1988, Seiten 379-384.
Navarro et al., "Tuning Diketodioxinone Reactivity: Biomimetic Synthesis of the Resorcylate Antibiotic Fungal Metabolites ent -W1278A, -B, and -C, Using Iterative Aromatization Reactions", Journal of Organic Chemistry, Bd. 74, Nr. 21, Nov. 6, 2009, Seiten 8139-8142, XP055658597.
Sridharan et al., "Mid and High-Yielding Synthesis of [beta]-Keto Esters and [beta]-Ketoamides", Synthesis, Bd. 2010, Nr. 06, Mar. 1, 2010, Seiten 1053-1057, XP055658643.
Florian et al., "The control of Novozym 435 chemoselectivity and specificity by the solvents in acylation reactions of amino-alcohols", Journal of Molecular Catalysis B: Enzymatic, Bd. 95, Seiten 99-110.
Wu et al., "Advances in lipase-catalyzed reactions in solvent-free systems", Journal of Molecular Catalysis (China), vol. 20, Issue No. 6, pp. 597-603.

* cited by examiner

*Primary Examiner* — James H Alstrum-Acevedo
*Assistant Examiner* — Carolyn L. Ladd
(74) *Attorney, Agent, or Firm* — Edward E. Sowers; Brannon Sowers & Cracraft PC

(57) ABSTRACT

The invention relates to a method for producing optionally functionalized acyl-capped (acyl-blocked) 3-hydroxybutyric acids and their salts and esters as well as to the products thus obtained and their use.

8 Claims, No Drawings

PROCESS FOR PREPARING ACYL-CAPPED 3-HYDROXYCARBOXYLIC ACIDS AND THEIR SALTS AND ESTERS

CROSS-REFERENCES TO RELATED APPLICATIONS

This application is a National Stage filing of International Application PCT/EP 2019/065275 filed Jun. 12, 2019, entitled "METHOD FOR PRODUCING ACYL-CAPPED 3-HYDROXYCARBOXYLIC ACIDS AND THEIR SALTS AND ESTERS". The subject application claims priority to PCT/EP 2019/065275 and incorporates all by reference herein, in its entirety.

BACKGROUND OF THE INVENTION

The present invention relates to the field of keto bodies and related metabolism and the therapy of related diseases.

Especially, the present invention relates to a method for producing optionally functionalized acyl-capped or acyl-blocked 3-hydroxybutyric acids and their salts and esters, as well as the reaction products thus obtainable or thus prepared (i. e. optionally functionalized acyl-capped or acyl-blocked 3-hydroxybutyric acids and their salts and esters) and their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i. e. optionally functionalized acyl-capped or acyl-blocked 3-hydroxybutyric acids and their salts and esters) obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i. e. optionally functionalized acyl-capped or acyl-blocked 3-hydroxybutyric acids and their salts and esters) obtainable or produced according to the inventive method, as well as their applications or uses.

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetacetate or 3-oxobutyrate) and acetone as well as 3-hydroxybutyric acid (hereinafter also synonymously referred to as beta-hydroxybutyric acid or BHB or 3-BHB) or its salt (i. e. 3-hydroxybutyrate or beta-hydroxybutyrate), the latter being the most important of the three aforementioned compounds. 3-Hydroxybutyric acid or its salt occurs physiologically as the (R)-enantiomer, i. e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoAsynthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric acid or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i. e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i. e. the metabolic conversion of caproic, caprylic and capric acid (i. e. of saturated linear $C_6$-, $C_8$- and $C_{10}$-fatty acids) from the corresponding triglycerides is intended.

Basically, however, from a pharmaceutical and clinical point of view, 3-hydroxybutyric acid as well as acetoacetate as a physiological precursor of 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid as well as for acetoacetate (and thus for 3-hydroxybutyric acid or its salts, which are physiologically obtainable by reduction of acetoacetate).

| Indication | Therapeutic effect |
|---|---|
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |
| Disorders of fatty acid oxidation (e.g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts as well as to acetoacetate (and thus physiologically to 3-hydroxybutyric acid and its salts), especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i. e. beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that optionally functionalized acyl-capped or acyl-blocked 3-hydroxybutyric acids and their salts and esters, especially the esters of optionally functionalized acyl-capped or acyl-blocked 3-hydroxybutyric acids, represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing optionally functionalized acyl-capped (acyl-blocked) 3-hydroxybutyric acid (beta-hydroxybutyric acid, BHB or 3-BHB) or its salts or esters.

Furthermore, the present invention relates—according to a second aspect of the present invention—to a reaction product obtainable according to the inventive method or an optionally functionalized acyl-capped (acyl-blocked) 3-hydroxybutyric acid (beta-hydroxybutyric acid, BHB or 3-BHB) or its salt or ester or a mixture of at least two, especially at least three optionally functionalized acyl-capped (acyl-blocked) 3-hydroxybutyric acids (beta-hydroxybutyric acid, BHB or 3-BHB) or their salts or esters obtainable in this regard.

Likewise, the present invention—according to a third aspect of the present invention—relates to a pharmaceutical composition, especially a drug or medicament.

Furthermore, the present invention—according to a fourth aspect of the present invention—relates to an inventive reaction product or an inventive optionally functionalized acyl-capped (acyl-blocked) 3-hydroxybutyric acid (beta-hydroxybutyric acid, BHB or 3-BHB) or its salt or ester or an inventive mixture of at least two, especially at least three optionally functionalized acyl-capped (acyl-blocked) 3-hydroxybutyric acids (beta-hydroxybutyric acid, BHB or 3-BHB) or their salts or esters for the prophylactic and/or therapeutic treatment or for use in the prophylactic and/or therapeutic treatment of diseases of the human or animal.

Furthermore, the present invention—according to a fifth aspect of the present invention—relates to the use of an inventive reaction product or an inventive optionally functionalized acyl-capped (acyl-blocked) 3-hydroxybutyric acid (beta-hydroxybutyric acid, BHB or 3-BHB) or its salt or ester or an inventive mixture of at least two, especially at least three optionally functionalized acyl-capped (acyl-blocked) 3-hydroxybutyrics acid (beta-hydroxybutyric acid, BHB or 3-BHB) or their salts or esters for the prophylactic and/or therapeutic treatment or for producing a medicament for the prophylactic and/or therapeutic treatment of diseases of the human or animal body.

Furthermore, the present invention—according to a sixth aspect of the present invention—relates to the use of an inventive reaction product or an inventive optionally functionalized acyl-capped (acyl-blocked) 3-hydroxybutyric acid (beta-hydroxybutyric acid, BHB or 3-BHB) or its salt or ester or an inventive mixture of at least two, especially at least three optionally functionalized acyl-capped (acyl-blocked) 3-hydroxybutyric acids (beta-hydroxybutyric acid, BHB or 3-BHB) or their salts or esters.

Furthermore, the present invention—according to a seventh aspect of the present invention—relates to a food and/or food product.

Finally, the present invention—according to an eighth aspect of the present invention—relates to the use of an inventive reaction product or an inventive optionally functionalized acyl-capped (acyl-blocked) 3-hydroxybutyric acid (beta-hydroxybutyric acid, BHB or 3-BHB) or its salt or ester or of an inventive mixture of at least two, especially at least three optionally functionalized acyl-capped (acyl-blocked) 3-hydroxybutyric acids (beta-hydroxybutyric acid, BHB or 3-BHB) or their salts or esters in a food and/or a food product.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

Additionally, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject-matter of the present invention—according to a first aspect of the present invention—is a method for producing acyl-capped (acyl-blocked) 3-hydroxybutyric acid (beta-hydroxybutyric acid, BHB and/or 3-BHB) or its salt or ester, wherein at least one compound of the general formula (I)

$$CH_3—CH(OH)—CH_2—C(O)OR^1 \quad (I)$$

wherein, in the general formula (I), the radical $R^1$ represents hydrogen or $C_1$-$C_4$-alkyl, especially $C_1$-$C_4$-alkyl, preferably methyl or ethyl, more preferably ethyl, is reacted with at least one compound of the general formula (II)

$$CH_3—C(O)—CH_2—C(O)OR^2 \quad (II)$$

wherein, in the compound of general formula (II), the radical $R^2$ represents $C_1$-$C_4$-alkyl, especially methyl or ethyl, preferably ethyl, so that, as a reaction product, there is obtained at least one acyl-capped (acyl-blocked) 3-hydroxybutyric acid or its salt or ester of the general formula (III)

$$CH_3—CH(OR^3)—CH_2—C(O)OR^1 \quad (III)$$

wherein, in the general formula (III), the radical $R^1$ has the meaning defined hereinabove and the radical $R^3$ represents a radical $CH_3—C(O)—CH_2—C(O)—$.

The inventive method thus results in a 3-hydroxybutyric acid or its salt or ester capped or blocked in the 3-position (=hydroxyl group position) with an acyl group. An acyl group is a functional group in organic chemistry with the general structure R—(C═O)—, wherein the radical R represents an organyl radical (alkyl, aryl or a heteroaromatic group etc.) or a hydrogen atom. The acyl group is formally derived from carboxylic acids, aldehydes and carboxylic acid chlorides in which an OH-group, a hydrogen atom or a chloride has been substituted by a radical R, respectively. An acylation refers to the introduction of such acyl group.

In the case that (as in the case of the invention) the acylation takes place at a hydroxyl group (OH-group) (namely at the OH-group located in the 3-position of the 3-hydroxybutyric acid), overall, an acyloxy group is formed which has the general structure R—(C═O)—O—.

According to the invention, an acyl-capped (=acyl-blocked) 3-hydroxybutyric acid is thus a butyric acid acylated in the 3-position or a butanoic acid acyloxylated in the 3-position.

As stated above, the applicant has, quite surprisingly, discovered that the acyl-capped (=acyl-blocked) 3-hydroxybutyric acids or their salts or esters (which may optionally also be functionalized, as described in detail hereinbelow) thus produced are efficient since physiologically compatible precursors and/or metabolites of free 3-hydroxybutyric acid or their salts or esters, which can also be used in larger quantities in pharmaceutical or clinical applications because they are physiologically compatible.

The above-mentioned optionally functionalized acyl-capped (=acyl-blocked) 3-hydroxybutyric acids or their salts or esters, which are accessible for the first time in an efficient manner through the production method according to the invention, thus represent a physiologically and pharmacologically relevant alternative to free 3-hydroxybutyric acid or its salts or esters.

The production of such compounds by means of conventional organic synthesis is complex and costly, since 3-hydroxybutyric acid has an increased tendency to polymerize and to undergo other undesirable side reactions (e. g. dehydration, decomposition, etc.). Within the scope of the present invention, it was possible for the first time to provide an efficiently working production method with which optionally functionalized acyl-capped (acyl-blocked) 3-hydroxybutyric acids or their salts or esters can be produced without undesired side reactions, especially in a single step.

The inventive method thus makes it possible for the first time to provide non-toxic optionally functionalized acyl-capped (acyl-blocked) 3-hydroxybutyric acids or their salts or esters from known, commercially available and above all physiologically harmless components or reactants (starting compounds). The resulting optionally functionalized acyl-capped 3-hydroxybutyric acids or their salts or esters can be broken down physiologically, especially in the stomach and/or intestine, and release or generate the target molecule "3-hydroxybutyric acid" or its salts (and also acetoacetate, which again can be further physiologically converted or reduced to 3-hydroxybutyric acid) as active ingredient or active component.

In addition, the aforementioned optionally functionalized acyl-capped (acyl-blocked) 3-hydroxybutyric acids or their salts or esters also comprise an acceptable taste to ensure compatibility even when administered orally in larger quantities over a longer period of time (e. g. administration of 50 g daily dose or more).

Furthermore, studies by the applicant show that the inventive optionally functionalized acyl-capped (acyl-blocked) 3-hydroxybutyric acids or their salts or esters are not only themselves efficient precursors or metabolites of free hydroxybutyric acid or its salts, but can also be used as starting materials for the synthesis of further precursors or metabolites of free hydroxybutyric acid or its salts (e. g. glycerides).

Similarly, the production method according to the invention makes it possible to provide the acyl-capped (acyl-blocked) 3-hydroxybutyric acids or their salts or esters free from toxic impurities.

During physiological cleavage in the stomach and/or intestine, the optionally functionalized acyl-capped (acyl-blocked) 3-hydroxybutyric acid is cleaved into the keto compounds 3-hydroxybutyric acid and 3-oxobutyrate (acetoacetate or acetacetate), which can be further reduced by the body to 3-hydroxybutyrate. Due to the presence of both 3-oxobutyrate radicals and 3-hydroxybutyrate radicals or 3-hydroxybutyric acid, there is a different rate of availability or release of the active ingredient 3-hydroxybutyric acid. Consequently, the inventive reaction product exhibits a retard effect. Overall, the optionally functionalized acyl-capped (acyl-blocked) 3-hydroxybutyric acid according to the invention thus exhibits two keto bodies with different rates of degradation.

Furthermore, a double capping (i. e. formation of a 3-BHB dimer which is subsequently capped by a keto compound according to the invention) can be achieved by a specific control of the reaction conditions, especially the reactant amounts and/or ratios, which in turn enables a longer-term availability of the active ingredient 3-hydroxybutyric acid.

In addition, with appropriate selection of the starting materials, the method can also be carried out enantioselectively. For example, according to the invention, the production method allows the biologically relevant form, i. e. the (R)-enantiomer, to be enriched or be obtained as not to burden the renal system of patients when administered orally (i. e. elimination via the kidneys). In principle, however, it is also possible, and under certain conditions may be useful, to enrich or to obtain the (S)-enantiomer.

In addition, the production method according to the invention, including optional further processing or purification steps, can be operated economically and can also be implemented on a large scale.

Especially, the inventive production method uses commercially available starting compounds and furthermore allows a relatively simple process management even in case of large-scale implementation. Furthermore, the starting compounds used are themselves physiologically compatible and even pharmaceutically active, so that any reactants still present can remain in the reaction product and no or hardly any purification method steps are necessary. In principle, however, it is possible and may be expedient under certain conditions, especially with regard to the organoleptic properties, to remove the reactants from the reaction product.

In contrast to conventional prior art production methods, the production method according to the invention does not use complex starting materials and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i. e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

The production method of acyl-capped (acyl-blocked) 3-hydroxybutyric acid according to the invention is illustrated in the following general reaction scheme (wherein $R^1$ and $R^2$ have the meaning defined hereinabove and "catalyst" denotes a catalyst):

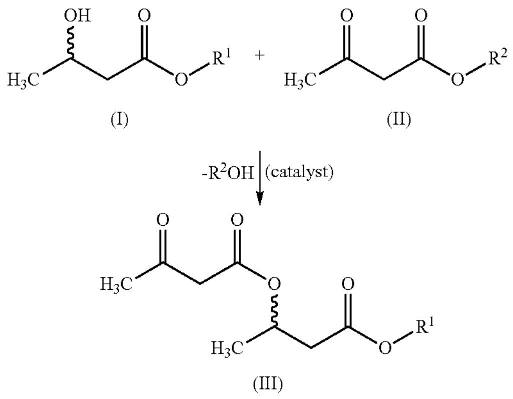

According to a particular embodiment of the present invention, the compound of the general formula (I) may be used either in racemic form or in the form of the (R)-enantiomer. The (R)-configuration refers to the chiral carbon atom in the 3-position of the compound of the general formula (I).

According to a preferred embodiment, the compound of the general formula (I) may be an ester (i. e. in the above general formula (I), the radical R represents $C_1$-$C_4$-alkyl or the radical $R^1$ does not represent hydrogen).

Especially, it may be preferred in the production method according to the invention that, in the above general formula (I), the radical $R^1$ represents ethyl. In other words, as compound of the general formula (I), 3-hydroxybutyric acid ethyl ester (ethyl 3-hydroxybutyrate) of the formula $CH_3$—$CH(OH)$—$CH_2$—$C(O)OC_2H_5$ may be used.

Moreover, according to the production method of the invention, it may be preferred that, in the general formula (II), the radical $R^2$ represents ethyl. In other words, in this embodiment, as compound of the general formula (II), 3-oxobutyric acid ethyl ester (ethyl 3-oxobutyrate) of the formula $CH_3$—$C(O)$—$CH_2$—$C(O)OC_2H_5$ is used.

According to a particular embodiment of the present invention, the present invention relates to a method for producing acyl-capped (acyl-blocked) 3-hydroxybutyric acid (beta-hydroxybutyric acid, BHB and/or 3-BHB) or its salt or ester, especially as defined hereinabove, wherein at least one compound of the formula (Ia)

$CH_3—CH(OH)—CH_2—C(O)OC_2H_5$ (Ia)

is reacted with at least one compound of formula (IIa)

$CH_3—C(O)—CH_2—C(O)OC_2H_5$ (IIa)

so that, as a reaction product, there is obtained at least one acyl-capped (acyl-blocked) 3-hydroxybutyric acid or its salt or ester of the formula (IIIa)

$CH_3—CH[O—C(O)—CH_2—C(O)—CH_3]—CH_2—C(O)OC_2H_5$ (IIIa).

The particularly preferred embodiment according to the invention, according to which the compounds of the general formula (I) and (II) are ethyl esters, is illustrated by the following reaction scheme:

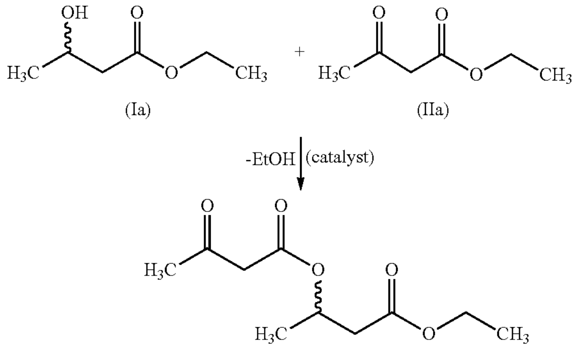

(Ia) (IIa) (IIIa)

This particular embodiment, according to which the compounds of the general formula (I) and (II) are ethyl esters, enables particularly efficient method control and high yields with minimized or suppressed by-product formation. Moreover, both the 3-hydroxybutyric acid 15 ethyl ester and the 3-oxobutyric acid ethyl ester are commercially available in larger quantities and can also be converted in an economically efficient manner. Especially, the 3-hydroxybutyric acid ethyl ester is more economically efficient than the free acid (i. e. 3-hydroxybutyric acid). Moreover, the starting compounds (i. e. ethyl 3-hydroxybutyric acid ester and ethyl 3-oxobutyric acid ester) can be obtained on a large scale, e. g. by Claisen condensation of ethyl acetate.

Especially, in the inventive method, the reaction is carried out in the absence of solvents and/or without any solvent. This means that the reaction is carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, the reaction can be carried out in the presence of a catalyst, especially an enzyme and/or a metal-containing and/or metal-based, acidic or basic catalyst, preferentially in the presence of an enzyme. In this particular embodiment, it is preferred that the catalyst is recycled after the reaction.

As mentioned above, according to the invention, the reaction can be carried out in the presence of an enzyme as a catalyst.

In this context, the enzyme can especially be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases.

Lipases in the sense of the present invention are especially enzymes which are capable of splitting free fatty acids from lipids such as glycerides (lipolysis).

Within the scope of the present invention, the enzyme used as catalyst can especially be derived from *Candida antarctica, Mucor miehei* (*Rhizomucor miehei*), *Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially from *Candida antarctica, Mucor miehei* (*Rhizomucor miehei*) and *Thermomyces lanuginosus.*

According to a specific embodiment, the enzyme can be used in immobilized form, especially immobilized on a carrier, preferentially on a polymeric carrier, preferably on a polymeric organic carrier, more preferably with hydrophobic properties, even more preferably on a poly(meth)acrylic resin-based carrier.

As explained hereinabove with respect to the use of a catalyst in general, when an enzyme is used as a catalyst, it is preferred to recycle the enzyme after the reaction.

If the reaction is carried out in the presence of an enzyme as a catalyst within the framework of the inventive production method, it is preferred if the reaction is carried out at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

In case of using an enzyme as a catalyst, the amount of the enzyme used can vary within a wide range. Especially, the enzyme can be used in amounts, based on the total amount of the starting compounds (I) and (II), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight. Nevertheless, it may be necessary to deviate from the above-mentioned amounts in individual cases or for specific applications without leaving the scope of the present invention.

If, according to a particular embodiment of the present invention, the reaction is carried out in the presence of an enzyme as a catalyst, the pressure range may also vary within a wide range. Especially, if the reaction is carried out in the presence of an enzyme as a catalyst, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the reaction can be carried out in the presence of a metal-containing and/or metal-based, acidic or basic catalyst.

According to this alternative embodiment of the present invention, according to which the reaction is carried out in the presence of a metal-containing and/or metal-based, acidic or basic catalyst, the catalyst can especially be selected from (i) basic catalysts, especially al*kali* or alkaline earth hydroxides and alkali or alkaline earth alcoholates, such as NaOH, KOH, LiOH, $Ca(OH)_2$, NaOMe, KOMe and Na(OBu-tert.), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

According to this embodiment, especially an alkali or alkaline earth alcoholate can be used as a catalyst.

Especially, also according to this embodiment it is preferred if the catalyst based on the metal-containing and/or metal-based, acidic or basic catalyst is recycled after the reaction.

Especially, it is also preferred in this embodiment if the catalyst based on the metal-containing and/or metal-based acidic or basic catalyst is recycled after the reaction.

If, according to this particular embodiment of the present invention the reaction is carried out in the presence of a metal-containing and/or metal-based, acidic or basic catalyst, the temperatures can be varied within a wide range. Especially, the reaction can be carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Furthermore, also according to this embodiment, the catalyst (i. e. the metal-containing and/or metal-based, acidic or basic catalyst) can also be varied within a wide quantity range: For example, the catalyst based on a metal-containing and/or metal-based, acidic or basic catalyst can be used in amounts, based on the total amount of the starting compounds (I) and (II), in the range of from 0.01 to 30% by weight, especially in the range of from 0.05 to 15% by weight, preferentially in the range of from 0.1 to 15% by weight, preferably in the range of from 0.2 to 10% by weight. Nevertheless, it is possible to deviate from the mentioned amounts for specific applications or individual cases without leaving the scope of the present invention.

If, according to this particular embodiment of the present invention, the reaction is carried out in the presence of a metal-containing and/or metal-based, acidic or basic catalyst, the pressure range can equally vary within a wide range: Especially, the reaction can be carried out in the presence of a metal-containing and/or metal-based, acidic or basic catalyst at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

As far as the quantity of starting materials or starting compounds is concerned, this can also be varied within a wide range.

Taking into account process economy and optimization of the course of the method, especially with regard to the minimization of by-products, it is advantageous if the compound of the general formula (II), based on the compound of the general formula (I), is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if the compound of the general formula (II) and the compound of the general formula (I) are used in a molar ratio of compound of the general formula (II)/compound of the general formular (I) in a range of from 1.1:1 to 10:1, preferably in a range of from 1.5:1 to 9:1, especially in a range of from 2:1 to 8:1, preferentially in a range of from 3:1 to 6:1. In this way, by-product formation, especially the formation of dimeric 3-hydroxybutyric acid and its acyl-capped derivatives, is efficiently counteracted.

In the production method according to the invention, during the reaction of the at least one compound of the general formula (I) with at least one compound of the general formula (II), a compound according to the general formula (IV)

$$R^2—OH \quad (IV)$$

is formed simultaneously, wherein the radical $R^2$ has the meaning defined hereinabove. Therefore, according to the invention, it may especially be provided that the compound according to general formula (IV) is especially continuously withdrawn from the reaction, especially by means of preferentially continuous removal by distillation. In this way, the reaction equilibrium is efficiently shifted to the side of the reaction products (i. e. the acyl-capped (acyl-blocked) 3-hydroxybutyric acid or its salt or ester of general formula (III)). Also, the formation of by-products is minimized or prevented in this way.

After the reaction, the reaction product obtained can be subjected to further purification or work-up steps.

In this context, the reaction of the at least one compound of the general formula (I) with at least one compound of the general formula (II) may be followed by a purification, especially by means of distillation and/or chromatography, preferentially by means of distillation.

Also, unreacted reactants or reactants still present and unreacted reaction by-products or reaction by-products still present, especially compounds according to the general formula (IV), can be separated off, especially distilled off.

Especially, in the context of the present invention, any reactants still present, especially reactants of the general formulae (I) and (II), may be recycled after their separation.

According to a particular embodiment of the inventive production method, it is possible especially to proceed in such a way that, after the reaction has been carried out, the reaction product (III) is at least partially, preferentially completely, functionalized at its radical $R^1$, preferentially by esterification or transesterification.

Especially, in the context of the present invention, the reaction may be followed by a partial, especially complete, functionalization of the reaction product (III) at its radical $R^1$, preferentially by esterification or transesterification.

In the context of the present invention, functionalization may be understood as the exchange or introduction of certain side groups or functional groups. An esterification takes place when the radical $R^1$ represents a hydrogen and thus the reaction product (III) is in the form of a carboxylic acid. This carboxylic acid is reacted with an alcohol in the course of esterification, so that an ester is formed with elimination of water. However, when the radical $R^1$ in the reaction product (III) represents $C_1$-$C_4$-alkyl, a transesterification takes place. In a transesterification, one ester is converted into another. The alcohol radical of an ester (i. e. in this case containing the $C_1$-$C_4$-alkyl radical) is replaced by another alcohol radical.

In this context, it is particularly preferred if the reaction product (III) is functionalized with at least one fatty alcohol (V), preferentially selected from $C_6$-$C_{30}$ fatty alcohols, preferably $C_{10}$-$C_{34}$-fatty alcohols, especially $C_{10}$-$C_{24}$-fatty alcohols.

According to a preferred embodiment of the present invention, the fatty alcohol (V) corresponds to the general formula (V')

$$R^4\text{—OH} \qquad (V')$$

wherein the radical $R^4$ represents a linear or branched, saturated or mono- or polyunsaturated aliphatic $C_6$-$C_{30}$-alkyl radical, preferentially $C_{10}$-$C_{30}$-alkyl radical, preferably $C_{10}$-$C_{24}$-alkyl radical, especially wherein the hydroxyl function (OH-function) is primary and/or terminal.

In this embodiment of the inventive method, it is particularly preferred if the radical $R^4$ represents a linear, saturated or mono- or polyunsaturated aliphatic $C_{10}$-$C_{24}$-alkyl radical, especially wherein the hydroxyl function (OH-function) is primary and/or terminal.

Especially, it is preferred if the radical $R^4$ represents a 1-decanyl radical, a 1-dodecanyl radical (lauryl radical), a 1-tetradecanyl radical (myristyl radical), a 1-hexadecanyl radical (cetyl radical), a 1-heptadecanyl radical (margaryl radical), a 1-octadecanyl radical (stearyl radical), a 1-eicosanyl radical (arachidyl radical), a 1-docosanyl radical (behenyl radical), a 1-tetracosanyl radical (ligoceryl radical), a 1-hexacosanyl radical (ceryl radical), a 1-octacosanyl radical (montanyl radical), a 1-tricontanyl radical (melissyl radical), a cis-9-hexadecene-1-yl radical (palmitoleyl radical), a cis-9-octadecene-1-yl radical (oleyl radical), a trans-9-octadecene-1-yl radical (elaidyl radical), a cis-11-octadecene-1-yl radical, a cis,cis-9,12-octadecadiene-1-yl radical (linoleyl radical) or a 6,9,12-octadecatriene-1-yl radical (γ-linolenyl radical), preferably a cis-9-octadecene-1-yl radical (oleyl radical).

According to a particular embodiment of the method according to the invention, it is preferred if the fatty alcohol (V) is selected from linear or branched, saturated or mono- or polyunsaturated aliphatic $C_6$-$C_{34}$-fatty alcohols, preferentially $C_{10}$-$C_{30}$-fatty alcohols, especially $C_{10}$-$C_{24}$-fatty alcohols, preferably with primary and/or terminal hydroxyl function (OH-function).

Especially, the fatty alcohol (V) which can be used in the inventive method can be selected from linear, saturated or mono- or polyunsaturated, aliphatic monohydric and preferably primary $C_6$-$C_{34}$-fatty alcohols, preferentially linear, saturated or mono- or polyunsaturated, aliphatic monohydric and preferably primary $C_{10}$-$C_{30}$-fatty alcohols, especially linear, saturated or mono- or polyunsaturated, aliphatic monohydric and preferably primary $C_{10}$-$C_{24}$-fatty alcohols.

According to a particular embodiment of the inventive method, the fatty alcohol (V) may be selected from the group of 1-decanol, 1-dodecanol (lauryl alcohol), 1-tetradecanol (myristyl alcohol), 1-hexadecanol (cetyl alcohol), 1-heptadecanol (margaryl alcohol), 1-octadecanol (stearyl alcohol), 1-eicosanol (arachidyl alcohol), 1-docosanol (behenylalcohol), 1-tetracosanol (ligoceryl alcohol), 1-hexacosanol (ceryl alcohol), 1-octacosanol (montanyl alcohol), 1-tricontanol (melissyl alcohol), cis-9-hexadecene-1-ol (palmitoleyl alcohol), cis-9-octadecene-1-ol (oleyl alcohol), trans-9-octadecene-1-ol (elaidyl alcohol), cis-11-octadecene-1-ol, cis,cis-9,12-octadecadiene-1-ol (linoleyl alcohol), 6,9,12-octadecatriene-1-ol (γ-linolenyl alcohol), and mixtures thereof, preferably cis-9-octadecene-1-ol (oleyl alcohol).

The above fatty alcohols (V) are commercially available chemical products or readily available from other sources.

In the particular embodiment of the present invention, according to which the reaction is followed by a partial, especially complete, functionalization of the reaction product (III) at its radical $R^1$, it is particularly preferred if the functionalization is carried out in the absence of solvents and/or without any solvent. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

Especially, according to this particular embodiment, it is preferred if the functionalization is carried out in the presence of a catalyst, especially an enzyme and/or a metal-containing and/or metal-based acidic or basic catalyst, preferentially in the presence of an enzyme. According to this particular embodiment it is preferred if the catalyst is recycled after the functionalization.

According to a preferred embodiment of the invention, the functionalization is carried out in the presence of an enzyme as a catalyst.

In this context, the enzyme may be selected from synthetases (ligases), catalases, esterases, lipases and combinations thereof.

In the context of the present invention, the enzyme used as catalyst may be derived from *Candida antarctica, Mucor miehei* (*Rhizomucor miehei*), *Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially of *Candida antarctica, Mucor miehei* (*Rhizomucor miehei*) and *Thermomyces lanuginosus.*

According to a particular embodiment, the enzyme may be used in immobilized form, especially immobilized on a carrier, preferentially on a polymeric carrier, preferably on a polymeric organic carrier, more preferably with hydrophobic properties, even more preferably on a poly(meth)acrylic resin-based carrier.

As previously stated in connection with the use of a catalyst in general, it is preferred to recycle the enzyme after the functionalization.

In the context of the present invention, the functionalization is carried out in the presence of an enzyme as a catalyst at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

Insofar as the functionalization in the production method according to the invention is carried out in the presence of an enzyme as catalyst, it is preferred if the enzyme is used in amounts, based on the total amount of compounds (III) and (V), in the range of from 0.001% by weight to 20% by weight, especially in the range of from 0.01% by weight to 15% by weight, preferentially in the range of from 0.1% by weight to 15% by weight, preferably in the range of from 0.5% by weight to 10% by weight.

When, according to a particular embodiment of the present invention, the functionalization is carried out in the presence of an enzyme as catalyst, the pressure range may also vary within a wide range. Especially, when the functionalization is carried out in the presence of an enzyme as a catalyst, the functionalization may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

According to an alternative embodiment of the present invention, the functionalization may be carried out in the presence of a metal-containing and/or metal-based, acidic or basic catalyst.

According to this alternative embodiment of the present invention, the catalyst in the context of the functionalization may be selected from (i) basic catalysts, especially alkali or alkaline earth hydroxides and alkali or alkaline earth alcoholates, such as NaOH, KOH, LiOH, $Ca(OH)_2$, NaOMe, KOMe and Na(OBu-tert.), (ii) acidic catalysts, especially mineral acids, and organic acids, such as sulfuric acid, hydrochloric acid, phosphoric acid, nitric acid, sulfonic acids, methane sulfonic acid, para-toluene sulfonic acid and carboxylic acids, (iii) Lewis acids, especially Lewis acids based on titanium, tin, zinc and aluminum compounds, such as titanium tetrabutylate, tin acids, zinc acetate, aluminum trichloride and aluminum tri-isopropyl, and (iv) heterogeneous catalysts, especially based on mineral silicates, germanates, carbonates and aluminum oxides, such as zeolites, montmorillonites, mordenites, hydrotalcites and aluminas, and combinations thereof.

Especially, an alkali or alkaline earth alcoholate may be used as a catalyst.

In this context, it is particularly preferred if the catalyst is recycled after the functionalization.

In the context of the present invention, it is preferred if the functionalization is carried out in the presence of a metal-containing and/or metal-based, acidic or basic catalyst at temperatures in the range of from 20° C. to 150° C., especially in the range of from 50° C. to 140° C., preferentially in the range of from 70° C. to 130° C., more preferably in the range of from 80° C. to 125° C., even more preferably in the range of from 100° C. to 120° C.

Insofar as the functionalization in the production method according to the invention is carried out in the presence of a metal-containing and/or metal-based, acidic or basic catalyst, it is preferred if the catalyst is used in amounts, based on the total amount of compounds (III) and (V), in the range of from 0.01% by weight to 30% by weight, especially in the range of from 0.05% by weight to 15% by weight, preferentially in the range of from 0.1% by weight to 15% by weight, preferably in the range of from 0.2% by weight to 10% by weight.

When, according to a particular embodiment of the present invention, the functionalization is carried out in the presence of a metal-containing and/or metal-based, acidic or basic catalyst, the pressure range may also vary within a wide range. Especially, when the functionalization is carried out in the presence of a metal-containing and/or metal-based, acidic or basic catalyst, it may be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

In the preferred embodiment according to the invention, according to which the reaction is followed by a partial, especially complete, functionalization of the reaction product (III) at its radical $R^1$, during the functionalization, a compound according to the general formula (VI)

$$R^1\text{—OH} \qquad \text{(VI)}$$

may especially be formed simultaneously, wherein, in the general formula (VI), the radical $R^1$ represents hydrogen or $C_1$-$C_4$-alkyl, especially $C_1$-$C_4$-alkyl, preferably methyl or ethyl, more preferably ethyl.

In this context, it is particularly preferred if the compound according to the general formula (VI) is withdrawn from the functionalization, especially continuously withdrawn, especially by means of preferentially continuous removal by distillation. In this way, the reaction equilibrium is efficiently shifted to the side of the reaction products (i. e. functionalization products). The formation of by-products is also minimized or prevented in this way.

A particularly preferred procedure according to the invention, according to which a functionalization of the reaction product (III) at its radical $R^1$ is provided following the reaction, is illustrated by the following reaction or synthesis scheme with the ethyl ester of acyl-capped (acyl-blocked) 3-hydroxybutyric acid (wherein the radical $R^4$ has the meaning defined hereinabove):

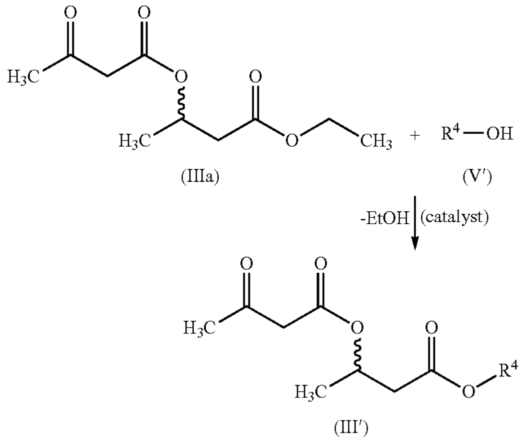

According to the method of the invention, as a reaction product, one or more optionally functionalized acyl-capped (acyl-blocked) 3-hydroxybutyric acids and/or their salts and/or esters of the general formula (III')

$$CH_3\text{—}CH(OR^3)\text{—}CH_2\text{—}C(O)OR^5 \qquad \text{(III')}$$

are formed, wherein, in the general formula (III'), the radical $R^3$ represents a radical $CH_3\text{—}C(O)\text{—}CH_2\text{—}C(O)\text{—}$ and the radical $R^5$ represents a radical $R^1$ as defined hereinabove and/or a radical $R^4$ as defined hereinabove.

According to a particular embodiment of the present invention, as a reaction product, one or more acyl-capped (acyl-blocked) 3-hydroxybutyric acids and/or their salts and/or esters of the general formula (III)

$$CH_3\text{—}CH(OR^3)\text{—}CH_2\text{—}C(O)OR^1 \qquad \text{(III)}$$

are formed, wherein, in the general formula (III), the radical $R^1$ represents hydrogen or $C_1$-$C_4$-alkyl, especially $C_1$-$C_4$-alkyl, preferably methyl or ethyl, more preferably ethyl, and the radical $R^3$ represents a radical $CH_3$—C(O)—$CH_2$—C(O)—.

According to another particular embodiment of the present invention, as a reaction product, one or more functionalized acyl-capped (acyl-blocked) 3-hydroxybutyric acids and/or their salts and/or esters of the general formula (III")

$$CH_3—CH(OR^3)—CH_2—C(O)OR^4 \quad (III")$$

are formed, wherein, in the general formula (III"), the radical $R^3$ represents a radical $CH_3$—C(O)—$CH_2$—C(O)— and the radical $R^4$ represents a linear or branched, saturated or mono- or polyunsaturated aliphatic $C_6$-$C_{30}$-alkyl radical, preferentially $C_{10}$-$C_{30}$-alkyl radical, preferably $C_{10}$-$C_{24}$-alkyl radical.

A further subject-matter—according to a second aspect of the present invention—is the reaction product (i. e. a (chemical) product or product mixture) obtainable according to the inventive method.

Especially, it is an object of the present invention to provide a reaction product (i. e. a (chemical) product or product mixture), which comprises one or more optionally functionalized acyl-capped (acyl-blocked) 3-hydroxybutyric acids and/or their salts and/or esters of the general formula (III')

$$CH_3—CH(OR^3)—CH_2—C(O)OR^5 \quad (III')$$

wherein, in the general formula (III'), the radical $R^3$ represents a radical $CH_3$—C(O)—$CH_2$—C(O)— and the radical $R^5$ represents a radical $R^1$, wherein the radical $R^1$ represents hydrogen or $C_1$-$C_4$-alkyl, especially $C_1$-$C_4$-alkyl, preferably methyl or ethyl, more preferably ethyl, or a radical $R^4$, wherein the radical $R^4$ represents a linear or branched, saturated or mono- or polyunsaturated aliphatic $C_6$-$C_{30}$-alkyl radical, preferentially $C_{10}$-$C_{30}$-alkyl radical, preferably $C_{10}$-$C_{24}$-alkyl radical.

According to a particular embodiment of the present invention, the reaction product may comprise one or more acyl-capped (acyl-blocked) 3-hydroxybutyric acids and/or their salts and/or esters of the general formula (III)

$$CH_3—CH(OR^3)—CH_2—C(O)OR^1 \quad (III)$$

wherein, in the general formula (III), the radical $R^1$ represents hydrogen or $C_1$-$C_4$-alkyl, especially $C_1$-$C_4$-alkyl, preferably methyl or ethyl, more preferably ethyl, and the radical $R^3$ represents a radical $CH_3$—C(O)—$CH_2$—C(O)—.

According to another particular embodiment of the present invention, the reaction product may comprise one or more functionalized acyl-capped (acyl-blocked) 3-hydroxybutyric acids and/or their salts and/or esters of the general formula (III")

$$CH_3—CH(OR^3)—CH_2—C(O)OR^4 \quad (III")$$

wherein, in the general formula (III"), the radical $R^3$ represents a radical $CH_3$—C(O)—$CH_2$—C(O)— and the radical $R^4$ represents a linear or branched, saturated or mono- or polyunsaturated aliphatic $C_6$-$C_{30}$-alkyl radical, preferentially $C_{10}$-$C_{30}$-alkyl radical, preferably $C_{10}$-$C_{24}$-alkyl radical.

According to another particular embodiment, the reaction product may especially comprise a mixture of at least two different optionally functionalized acyl-capped (acyl-blocked) 3-hydroxybutyric acids, especially as defined hereinabove.

According to a further particular embodiment, the reaction product may especially comprise a mixture of at least three different optionally functionalized acyl-capped (acyl-blocked) 3-hydroxybutyric acids, especially as defined hereinabove.

It is also an object of the present invention to provide an optionally functionalized acyl-capped (acyl-blocked) 3-hydroxybutyric acid and/or its salt and/or ester of the general formula (III')

$$CH_3—CH(OR^3)—CH_2—C(O)OR^5 \quad (III')$$

wherein, in the general formula (III'), the radical $R^3$ represents a radical $CH_3$—C(O)—$CH_2$—C(O)— and the radical $R^5$ represents a radical $R^1$, wherein the radical $R^1$ represents hydrogen or $C_1$-$C_4$-alkyl, especially $C_1$-$C_4$-alkyl, preferably methyl or ethyl, more preferably ethyl, or a radical $R^4$, wherein the radical $R^4$ represents a linear or branched, saturated or mono- or polyunsaturated aliphatic $C_6$-$C_{30}$-alkyl radical, preferentially $C_{10}$-$C_{30}$-alkyl radical, preferably $C_{10}$-$C_{24}$-alkyl radical.

A further object of the present invention is also an acyl-capped (acyl-blocked) 3-hydroxybutyric acid and/or its salt and/or ester, especially as described hereinabove, wherein the acyl-capped (acyl-blocked) 3-hydroxybutyric acid and/or its salts and/or esters corresponds to the general formula (III)

$$CH_3—CH(OR^3)—CH_2—C(O)OR^1 \quad (III)$$

wherein, in the general formula (III), the radical $R^1$ represents hydrogen or $C_1$-$C_4$-alkyl, especially $C_1$-$C_4$-alkyl, preferably methyl or ethyl, more preferably ethyl, and the radical $R^3$ represents a radical $CH_3$—C(O)—$CH_2$—C(O)—.

Again, another object of the present invention is a functionalized acyl-capped (acyl-blocked) 3-hydroxybutyric acid and/or its salt and/or ester, especially as defined hereinabove, wherein the functionalized acyl-capped (acyl-blocked) 3-hydroxybutyric acid and/or its salts and/or esters corresponds to the general formula (III")

$$CH_3—CH(OR^3)—CH_2—C(O)OR^4 \quad (III")$$

wherein, in the general formula (III"), the radical $R^3$ represents a radical $CH_3$—C(O)—$CH_2$—C(O)— and the radical $R^4$ represents a linear or branched, saturated or mono- or polyunsaturated aliphatic $C_6$-$C_{34}$-alkyl radical, preferentially $C_{10}$-$C_{30}$-alkyl radical, preferably $C_{10}$-$C_{24}$-alkyl radical.

A further object of the present invention according to this aspect of the invention is a mixture comprising at least two different optionally functionalized acyl-capped (acyl-blocked) 3-hydroxybutyric acids and/or their salts and/or esters, as defined hereinabove.

Especially, again a further object of the present invention according to this aspect of the invention is a mixture comprising at least three different optionally functionalized acyl-capped (acyl-blocked) 3-hydroxybutyric acids and/or their salts and/or esters, as defined hereinabove.

The reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, comprises a multitude of advantages and special features compared to the prior art:

As the applicant has surprisingly found out, the reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, is suitable as a precursor or metabolite of 3-hydroxybutyric acid or its salts, since, on the one hand, it is converted physiologically, especially in the gastrointestinal tract, to the keto-bodies 3-hydroxybutyric acid and 3-oxobutyrate (=acetoacetate or acetacetate), which is ultimately converted or reduced physiologically to 3-hydroxybutyric acid or its salts, and, on the other hand, it simultaneously comprises a good physiological compatibility or tolerability, especially with regard to non-toxicity and acceptable organoleptic properties. Especially, the sustained release of the physiologically active substance in the gastrointestinal tract is advantageous in the medical field, since the active substance 3-hydroxybutyric acid can thus be made available over a longer period of time, thus enabling ketosis therapy.

Therefore, the reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, are suitable as effective precursors or metabolites which physiologically provide direct or indirect access to 3-hydroxybutyric acid or its salts and to acetoacetate (and thus physiologically in turn to 3-hydroxybutyric acid or its salts), especially in the physiological metabolism of the human or animal body.

Thus, during the physiological cleavage in the stomach and/or intestine, the reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, is cleaved into the keto compounds 3-hydroxybutyric acid and 3-oxobutyrate (acetoacetate and acetacetate, respectively), which can be further reduced by the body to 3-hydroxybutyrate.

Due to the presence of both 3-oxobutyrate radicals and 3-hydroxybutyrate radicals or 3-hydroxybutyric acid, there is a different rate of availability or release of the active ingredient 3-hydroxybutyric acid. Consequently, the inventive reaction product has an intrinsic, further differentiated retard effect. For, overall, the inventive optionally functionalized acyl-capped (acyl-blocked) 3-hydroxybutyric acid or its salt or ester thus exhibits two keto bodies with different rates of degradation.

The inventive method thus enables, for the first time, the production of non-toxic, optionally functionalized acyl-capped (acyl-blocked) 3-hydroxybutyric acids as well as their salts and esters from components or reactants (starting compounds) which are known per se, commercially available and, above all, physiologically harmless. The resulting optionally functionalized acyl-capped 3-hydroxybutyric acids and their salts and esters can be physiologically cleaved, especially in the stomach and/or in the intestine, and release or generate the target molecule "3-hydroxybutyric acid" or its salts (and also acetoacetate, which in turn can be physiologically further converted or reduced to 3-hydroxybutyric acid) as active substance or active component.

Furthermore, the reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, is readily accessible or available on a synthetic scale, even with the required pharmaceutical or pharmacological quality.

Additionally, the reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, may be provided in an enantiomerically pure or enantiomerically enriched form.

The reaction product obtainable according to the inventive method or the inventive reaction product as defined hereinabove, respectively, and/or the optionally functionalized acyl-capped (acyl-blocked) 3-hydroxybutyric acid obtainable according to the inventive production method or the inventive optionally functionalized acyl-capped (acyl-blocked) 3-hydroxybutyric acid as defined hereinabove, respectively, and/or the mixture, obtainable according to the inventive production method or the inventive mixture as defined hereinabove, respectively, thus represents an efficient pharmacological drug target in the context of keto-body therapy of the human or animal body.

In the following, the remaining aspects of the invention are explained in more detail.

A further subject-matter of the present invention—according to a third aspect of the present invention—is a pharmaceutical composition, especially a drug or medicament, which comprises a reaction product obtainable according to the inventive production method or the inventive reaction product as defined hereinabove, respectively, and/or an optionally functionalized acyl-capped (acyl-blocked) 3-hydroxybutyric acid or its salt or ester, obtainable according to the inventive production method or the inventive optionally functionalized acyl-capped (acyl-blocked) 3-hydroxybutyric acid or its salt or ester as defined hereinabove, respectively, and/or a mixture, obtainable according to the inventive production method or the inventive mixture as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject-matter of the present invention—according to a fourth aspect of the present invention—is a reaction product obtainable according to the inventive production method or the inventive reaction product as defined hereinabove, respectively, and/or an optionally functionalized acyl-capped (acyl-blocked) 3-hydroxybutyric acid or its salt or ester, obtainable according to the inventive production method or the inventive optionally functionalized acyl-capped (acyl-blocked) 3-hydroxybutyric acid or its salt or ester as defined hereinabove, respectively, and/or a mixture, obtainable according to the inventive production method or the inventive mixture as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a fifth aspect of the present invention—is the use of a reaction product as defined hereinabove, respectively, and/or the use of an optionally functionalized acyl-capped (acyl-blocked) 3-hydroxybutyric acid or its salt or ester as defined hereinabove, respectively, and/or the use of a mixture as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a sixth aspect of the present invention—is the use of a reaction product obtainable according to the inventive production method or the inventive reaction product as defined hereinabove, respectively, and/or the use of an optionally functionalized acyl-capped (acyl-blocked) 3-hydroxybutyric acid or its salt or ester, obtainable according to the inventive production method or the inventive optionally functionalized acyl-capped (acyl-blocked) 3-hydroxybutyric acid or its salt or ester as defined hereinabove, respectively, and/or the use of a mixture, obtainable according to the inventive production method or the inventive mixture as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a seventh aspect of the present invention—is a food and/or a food product, which comprises a reaction product obtainable according to the inventive production method or the inventive reaction product as defined hereinabove, respectively, and/or an optionally functionalized acyl-capped (acyl-blocked) 3-hydroxybutyric acid or its salt or ester, obtainable according to the inventive production method or the optionally functionalized acyl-capped (acyl-blocked) 3-hydroxybutyric acid or its salt or ester as defined hereinabove, respectively, and/or a mixture, obtainable according to the inventive production method or the inventive mixture as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an eighth aspect of the present invention—is the use of a reaction product obtainable according to the inventive production method or the inventive reaction product as defined hereinabove, respectively, and/or an optionally functionalized acyl-capped (acyl-blocked) 3-hydroxybutyric acid or its salt or ester, obtainable according to the inventive production method or the optionally functionalized acyl-capped (acyl-blocked) 3-hydroxybutyric acid or its salt or ester as defined hereinabove, respectively, and/or a mixture, obtainable according to the inventive production method or the inventive mixture as defined hereinabove, respectively, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Abbreviations Used

3-BHB=3-hydroxybutyric acid or 3-hydroxybutyric acid radical (3-hydroxybutyrate radical)

3-BHB-FS=3-hydroxybutyric acid (free acid)

3-BHB dimer ethyl ester=dimer of 3-BHB ethyl ester 3-acetylaceto-BHB-FS=3-acetylacetobutyric acid (free acid)

acetylaceto-$BHB_2$-ethyl ester=dimer of 3-BHB-ethyl ester capped with ethyl acetoacetate

Examples of Production

The inventive production method is illustrated by the following examples. The relevant general reaction schemes are shown and explained in the general description section.

Production of 3-acetylaceto-BHB-Ethyl Ester and Application Tests 52 g ethyl 3-oxobutyric acid ester (ethyl acetoacetate or acetoacetic acid ester) and 26 g ethyl 3-hydroxybutyric acid ester (ethyl 3-BHB ester) are provided in a 100-ml-multi-neck flask with dephlegmator (partial condenser) and distillation bridge.

At a temperature of 50° C. and under vacuum, 0.8 g immobilized enzyme (CALB lipase on polymer support, derived from *Candida antarctica*, e. g. Novozym® 435) is added. The reaction mixture is allowed to react for 6 h under stirring. The ethanol produced during the reaction is continuously distilled off. Subsequently, the enzyme is filtered off and excess 3-oxobutyric acid ethyl ester as well as excess 3-hydroxybutyric acid ethyl ester is distilled off under vacuum and recycled.

The reaction product obtained is a 3-acetylacetobutyric acid ethyl ester (3-acetylaceto-BHB ethyl ester) and, according to analytical analysis, consists of the following composition: >90% 3-acetylaceto-BHB ethyl ester (reaction by-products: 3-BHB dimer ethyl ester <5% and acetylaceto-BHB dimer ethyl ester <5%).

Characterization is performed by gas chromatography (GC) and GC-MS analysis (gas chromatography with mass spectrometry coupling).

The taste of 3-acetylaceto-BHB ethyl ester is significantly less unpleasant and bitter than that of pure 3-BHB ethyl ester or even pure 3-hydroxybutyric acid.

Cleavage experiments (cleavage experiments) with 3-acetylaceto-BHB ethyl esters in a gastric or intestinal medium (FaSSGF medium simulating the stomach or FaSSIF medium simulating the intestinal tract), each in the presence or absence of pancreatin, demonstrate cleavage to 3-BHB in the free form. These cleavage experiments prove that acyl-capped (acyl-blocked) 3-hydroxybutyric acid or its salts or esters, here specifically 3-acetylaceto-BHB ethyl esters, are efficient precursors or metabolites of free 3-hydroxybutyric acid or its salts and further keto bodies (here: acetoacetate), particularly with regard to their intended effect, wherein these compounds are also present in physiologically tolerable or physiologically compatible form.

Further Production of 3-acetylaceto-bhb ethyl Ester 30 g ethyl 3-oxobutyric acid ester (ethyl acetoacetate or acetoacetic acid ester) and 15.25 g ethyl 3-hydroxybutyric acid ester (ethyl 3-BHB ester) are provided in a 100-ml-multi-neck flask equipped with a dephlegmator (partial condenser) and a distillation bridge.

At a temperature of 50° C. and under vacuum, 0.46 g immobilized enzyme (CALB lipase on polymer support, derived from *Candida antarctica*, e. g. Novozym® 435) is added. The reaction mixture is allowed to react for 6 h under stirring. The ethanol produced during the reaction is continuously distilled off. The enzyme is then filtered off and excess ethyl 3-oxobutyric acid ester and excess ethyl 3-hydroxybutyric acid ester are distilled off under vacuum and then recycled.

Characterization is performed by gas chromatography (GC) and GC-MS analysis (gas chromatography with mass spectrometry coupling).

The conversion/time curve is determined by means of GC. Based on the quantities determined by GC, a conversion to the desired product (here: 3-acetylaceto-BHB ethyl ester) can be detected. As the reaction time progresses, there is also a conversion of the resulting 3-BHB dimer ethyl ester with ethyl acetoacetate to acetylaceto-$BHB_2$ ethyl ester (acyl-capped 3-BHB dimer ethyl ester) as a by-product (<1%).

Further Production Examples

The experiments are repeated with sodium methanolate (NaOMe) as a catalyst instead of the enzyme and at temperatures between 10° and 120° C. Comparable results are obtained. Purification and analysis are carried out in the same way.

Again More Production Examples

In a further series of experiments, the influence of the molar ratio of the starting compounds is investigated with regard to the formation of by-products (analytically examined using the two by-products "3-BHB dimer ethyl ester" and "acetylaceto-$BHB_2$ ethyl ester").

It is shown that a molar excess of 3-oxobutyric acid ethyl ester (ethyl acetoacetate or acetoacetic ester) in relation to the other reactant 3-hydroxybutyric acid ethyl ester (3-BHB ethyl ester) counteracts by-product formation.

In a first series of investigations, an acetoacetic ester/3-BHB ethyl ester molar ratio in the range of from 1.5:1 to 9:1 is shown to be particularly efficient in terms of by-product formation and is also still process economical. Particularly good results are observed in a second series of investigations for an acetoacetic ester/3-BHB ethyl ester molar ratio in the range of from 2:1 to 8:1.

Functionalization 150 g 3-acetylaceto-BHB-ethyl ester, 158 g 1-decanol and 2.9 g immobilized enzyme (CALB lipase on polymer support, derived from *Candida antarctica*, e. g. Novozym® 435 from Sigma-Aldrich or Merck or Lipozym®435 from Strem Chemicals, Inc.) are provided.

The reaction mixture is reacted under stirring at 70° C. and under vacuum (<500 mbar) for 7 h. The ethanol produced during the reaction is continuously distilled off. The enzyme is then filtered off and the excess 3-acetylaceto-BHB-ethyl ester or the excess 1-decanol is distilled off under vacuum. The radical obtained is steamed for 2 to 4 h under high vacuum (steam temperature 160° C.). Pure 3-acetylaceto-BHB-decyl ester is obtained.

Further Functionalization 150 g 3-acetylaceto-BHB-ethyl ester, 270 g oleyl alcohol (purity: 85%) and 4.0 g immobilized enzyme (CALB lipase on polymer support, derived from *Candida antarctica*, e. g. Novozym® 435 from Sigma-Aldrich or Merck or Lipozym® 435 from Strem Chemicals, Inc.) are provided.

The reaction mixture is reacted under stirring at 70° C. and under vacuum (<500 mbar) for 7 h. The ethanol produced during the reaction is continuously distilled off. The enzyme is then filtered off and the product 3-acetylaceto-BHB-oleyl ester is obtained in vacuo by multiple distillation. If necessary, the residue obtained is steamed in high vacuum for 2 to 4 h (steam temperature 160° C.). Pure 3-acetylaceto-BHB-oleyl ester is obtained.

Again Further Functionalization Examples

The above enzyme-catalyzed functionalizations are also carried out accordingly with other fatty alcohols (namely with cetyl alcohol, margaryl alcohol, stearyl alcohol, behenyl alcohol, melissyl alcohol, palmitoleyl alcohol and linoleyl alcohol, respectively). The corresponding 3-acetylaceto-BHB fatty alcohol esters are each obtained as pure substances.

Once Again Further Functionalization Examples

The previous experiments are repeated, however, with sodium methanolate (NaOMe) as a catalyst (1% by weight) instead of the enzyme and at temperatures between 10° and 120° C. Comparable results are obtained. Purification and separation are carried out in the same way.

Physiological Application Tests: In-Vitro Digestion Tests

Digestion Experiments (Splitting or Cleavage Experiments) of Inventive 3-acetylaceto-BHB Esters (i. e. Ethyl Esters and Fatty Alcohol Esters of 3-acetylacetobutyric Acid)

By means of cleavage experiments, it is shown that 3-acetylaceto-BHB ethyl esters prepared according to the invention as well as the functionalized derivatives (i. e. 3-acetylaceto-BHB fatty alcohol esters), including the reaction by-products such as dimers, etc., can be cleaved in the human gastrointestinal tract.

In each case, purified 3-acetylaceto-BHB ethyl esters obtained by the inventive method and the functionalized derivatives (i. e. 3-acetylaceto-BHB fatty alcohol esters) are used as the test substance.

Esters tested:

3-Acetylaceto-BHB ethyl ester
3-Acetylaceto-BHB decyl ester
3-Acetylaceto-BHB oleyl ester
3-Acetylaceto-BHB cetyl ester
3-Acetylaceto-BHB-margaryl ester
3-Acetylaceto-BHB stearyl ester
3-Acetylaceto-BHB behenyl ester
3-Acetylaceto-BHB melissyl ester
3-Acetylaceto-BHB palmitoyl ester
3-Acetylaceto-BHB linoleyl ester For the cleavage experiments under near-body conditions two media are investigated:

FaSSGF, which simulates the stomach

FaSSIF, which simulates the intestinal tract Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that the samples hydrolyze under FaSSGF conditions with Panzytrat® and without Panzytrat®; this is mainly due to the low pH value (pH=1.6) of the medium. Under FaSSIF conditions, a lower conversion using Panzytrat® takes place.

The experiments prove that the 3-acetylaceto-BHB ethyl ester as well as their fatty alcoholfunctionalized derivatives each represent a suitable physiological precursor for the keto bodies 3-hydroxybutyric acid as well as acetoacetate (and thereby ultimately 3-hydroxybutyric acid) for use in the corresponding keto body therapies.

Further Digestion Experiments (Cleavage Experiments) of Inventive

3-Acetylaceto-BHB Ethyl Esters and Functionalized Derivatives Thereof Cleavage experiments with pancreatin 2 g of each of the 3-acetoacetate-BHB ethyl esters prepared as described above and the 3-acetoacetate-BHB fatty alcohol esters prepared as described above are dissolved in 50 g water and 0.5 g (1% by weight) pancreatin is added. The pancreatin is used in the form of the commercially available product Panzytrat® 40,000 from the Allergan company. The whole mixture is stirred on a hot plate at 50° C.; the course of the reaction is determined and monitored by continuously recording the acid number over time. The acid number increases over the observation period (cleavage of the 3-acetylaceto-BHB ester to the free 3-hydroxybutyric acid and acetoacetate, which in turn can be physiologically reduced to 3-BHB and to 3-hydroxybutyrate, respectively). The conversion/time course of the aqueous cleavage of the esters according to the invention by means of pancreatin, including the increase of the acid number over time, demonstrates the desired decomposition of the reactant or reactant mixture to the free acid. This is confirmed by corresponding analytics. The experiment proves that both the 3-acetylaceto-BHB ethyl ester according to the invention and the functionalized derivatives (i. e. 3-acetylaceto-BHB fatty alcohol esters) are suitable physiological precursors for 3-hydroxybutyric acid for the corresponding keto body therapies. The experiments are repeated and verified using each ester in its pure form. Comparable results are obtained, i. e. both the 3-acetylaceto-BHB ethyl esters and also the functionalized derivatives are each cleaved by pancreatin.

The previously described cleavage experiments prove that 3-acetylaceto-BHB ethyl esters as well as the functionalized derivatives (i. e. 3-acetylaceto-BHB fatty alcohol esters) are efficient precursors or metabolites of free 3-hydroxybutyric acid or its salts, especially with regard to their intended effect, which are also present in physiologically tolerable or physiologically compatible form.

The invention claimed is:

1. A functionalized acyl-capped 3-hydroxybutyric ester, wherein the functionalized acyl-capped 3-hydroxybutyric ester corresponds to general formula (III")

$$CH_3—CH(OR^3)—CH_2—C(O)OR^4 \quad (III")$$

wherein, in the general formula (III"), the radical $R^3$ represents a radical $CH_3—C(O)—CH_2—C(O)—$ and the radical $R^4$ represents a linear or branched, saturated or mono- or polyunsaturated aliphatic $C_6$-$C_{30}$-alkyl radical.

2. The functionalized acyl-capped 3-hydroxybutyric ester according to claim 1, wherein the functionalized acyl-capped 3-hydroxybutyric ester corresponds to general formula (III")

$$CH_3—CH(OR^3)—CH_2—C(O)OR^4 \quad (III")$$

wherein, in the general formula (III"), the radical $R^3$ represents a radical $CH_3—C(O)—CH_2—C(O)—$ and the radical $R^4$ represents a linear or branched, saturated or mono- or polyunsaturated aliphatic $C_{10}$-$C_{30}$-alkyl radical.

3. The functionalized acyl-capped 3-hydroxybutyric ester according to claim 1, wherein the functionalized acyl-capped 3-hydroxybutyric ester corresponds to general formula (III")

$$CH_3—CH(OR^3)—CH_2—C(O)OR^4 \quad (III")$$

wherein, in the general formula (III"), the radical $R^3$ represents a radical $CH_3—C(O)—CH_2—C(O)—$ and the radical $R^4$ represents a linear or branched, saturated or mono- or polyunsaturated aliphatic $C_{10}$-$C_{24}$-alkyl radical.

4. A mixture comprising at least two different functionalized acyl-capped 3-hydroxybutyric esters, as defined in claim 1.

5. A pharmaceutical composition comprising at least one functionalized acyl-capped 3-hydroxybutyric ester, as defined in claim 1.

6. The pharmaceutical composition according to claim 5, wherein the pharmaceutical composition is a drug or medicament.

7. A food or a food product comprising at least one functionalized acyl-capped 3-hydroxybutyric ester, as defined in claim 1.

8. A functionalized acyl-capped 3-hydroxybutyric ester, wherein the functionalized acyl-capped 3-hydroxybutyric ester corresponds to general formula (III")

$$CH_3—CH(OR^3)—CH_2—C(O)OR^4 \quad (III")$$

wherein, in the general formula (III"), the radical $R^3$ represents a radical $CH_3—C(O)—CH_2—C(O)—$ and the radical $R^4$ represents a linear or branched, saturated or mono- or polyunsaturated aliphatic $C_{10}$-$C_{30}$-alkyl radical.

* * * * *